US010855323B2

(12) United States Patent
Greiner

(10) Patent No.: US 10,855,323 B2
(45) Date of Patent: *Dec. 1, 2020

(54) MEDICAL DEVICE CASE

(71) Applicant: Alexander N. Greiner, San Diego, CA (US)

(72) Inventor: Alexander N. Greiner, San Diego, CA (US)

(73) Assignee: EpiClip, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/435,386

(22) Filed: Jun. 7, 2019

(65) Prior Publication Data
US 2019/0296787 A1 Sep. 26, 2019

Related U.S. Application Data

(63) Continuation of application No. 15/432,813, filed on Feb. 14, 2017, now Pat. No. 10,320,439, which is a
(Continued)

(51) Int. Cl.
H04B 1/3888 (2015.01)
B65D 85/00 (2006.01)
(Continued)

(52) U.S. Cl.
CPC .......... *H04B 1/3888* (2013.01); *A45C 11/00* (2013.01); *A45C 15/00* (2013.01); *A61J 1/03* (2013.01);
(Continued)

(58) Field of Classification Search
CPC ... A45C 11/00; A45C 15/00; A45C 2011/002; A45C 2011/007; A61J 1/03; A61J 1/16; A61J 2205/30; A61M 15/0086; A61M 2209/06; A61M 5/002; B65D 50/00; B65D 55/02; B65D 85/70; H04B 1/3877; H04B 1/3888; H04M 1/0249; H04M 1/21
See application file for complete search history.

(56) References Cited

U.S. PATENT DOCUMENTS 8,833,379 B1 9/2014 Kaplan
9,138,539 B1 9/2015 Friedman
(Continued)

OTHER PUBLICATIONS

"I just filed a patent that links an epipen with a smartphone, should I dance with investors or offer it for free to charitable orgs like World Allergy Organization (or both)?" *Quora—The best answer to any question*. Quora, Inc. Jan. 7, 2015. Web. Retrieved Aug. 18, 2016. 6 pages. <<https://www.quora.com/I-just-filed-a-patent-that-links-an-epipen-with-a-smartphone-should-I-dance-with-investors-or-offer-it-for-free-to-charitable-orgs-like-World-Allergy-Organization-or-both>>.
(Continued)

*Primary Examiner* — Timothy X Pham
(74) *Attorney, Agent, or Firm* — Mintz Levin Cohn Ferris Glovsky and Popeo, P.C.; Andrew D. Skale

(57) ABSTRACT

This disclosure relates generally to embodiments disclosing a case designed to contain both a smartphone and a medical device, such as an epinephrine auto-injector. The case contains allows both the smartphone and the medical device to remain within the case while the case is being transported. The case may also include a release mechanism for releasing the medical device from the case.

20 Claims, 9 Drawing Sheets

Related U.S. Application Data continuation of application No. 14/637,259, filed on Mar. 3, 2015, now Pat. No. 9,590,683.

(60) Provisional application No. 61/946,888, filed on Mar. 3, 2014.

(51) Int. Cl.
*B65D 50/00* (2006.01)
*B65D 55/02* (2006.01)
*A61J 1/03* (2006.01)
*A61J 1/16* (2006.01)
*H04M 1/21* (2006.01)
*A45C 11/00* (2006.01)
*A45C 15/00* (2006.01)
*H04B 1/3877* (2015.01)
*A61M 5/00* (2006.01)
*A61M 15/00* (2006.01)
*H04M 1/02* (2006.01)

(52) U.S. Cl.
CPC ............... *A61J 1/16* (2013.01); *A61M 5/002* (2013.01); *A61M 15/0086* (2013.01); *B65D 50/00* (2013.01); *B65D 55/02* (2013.01); *B65D 85/70* (2013.01); *H04B 1/3877* (2013.01); *H04M 1/0249* (2013.01); *H04M 1/21* (2013.01); *A45C 2011/002* (2013.01); *A45C 2011/007* (2013.01); *A61J 2205/30* (2013.01); *A61M 2209/06* (2013.01)

(56) References Cited

U.S. PATENT DOCUMENTS

| | | | |
|---|---|---|---|
| 9,590,683 B2 | 3/2017 | Greiner | |
| 10,320,439 B2 | 6/2019 | Greiner | |
| 2003/0038047 A1 | 2/2003 | Sleva et al. | |
| 2003/0106917 A1 | 6/2003 | Shetler et al. | |
| 2004/0155079 A1 | 8/2004 | Shetler et al. | |
| 2005/0241972 A1 | 11/2005 | Hassett | |
| 2006/0105821 A1 | 5/2006 | Goradesky et al. | |
| 2011/0005648 A1 | 1/2011 | Sa | |
| 2011/0089078 A1* | 4/2011 | Ziemba | A45C 1/04 206/570 |
| 2011/0094423 A1 | 4/2011 | DelloRusso, Jr. | |
| 2011/0192857 A1* | 8/2011 | Rothbaum | F16M 11/041 220/694 |
| 2012/0172803 A1* | 7/2012 | Hanson | A61M 5/1413 604/151 |
| 2013/0027867 A1* | 1/2013 | Lauder | G06F 1/1675 361/679.29 |
| 2013/0233741 A1 | 9/2013 | Caruth | |
| 2013/0316645 A1 | 11/2013 | Li et al. | |
| 2014/0049911 A1* | 2/2014 | Corbin | G06F 1/1643 361/679.58 |
| 2014/0228082 A1 | 8/2014 | Morrow et al. | |
| 2014/0326636 A1* | 11/2014 | Baschnagel | A61J 1/03 206/538 |
| 2014/0360898 A1 | 12/2014 | Kantor et al. | |
| 2016/0353849 A1* | 12/2016 | Macadaan | A45C 13/02 |
| 2019/0180898 A1* | 6/2019 | Lauder | G06F 1/1626 |

OTHER PUBLICATIONS

Ghoreshi, Kayvon. "Redesigning and Incorporating the EpiPen into a Smartphone Case." *Holster Scholar Projects*. University of Connecticut DigitalCommons@UConn. 2013. Web. 24 pages. Retrieved Aug. 18, 2016. <<http://digitalcommons.uconn.edu/srhonors_holster/14>>.

* cited by examiner

MEDICAL DEVICE CASE

CROSS-REFERENCES TO RELATED APPLICATIONS

This application is a continuation application of U.S. Non-Provisional application Ser. No. 15/432,813, filed Feb. 14, 2017, which is a continuation application of U.S. Non-Provisional application Ser. No. 14/637,259, filed Mar. 3, 2015, now patented as U.S. Pat. No. 9,590,683, which claims priority from U.S. Provisional Patent Application No. 61/946,888, filed Mar. 3, 2014, which are hereby incorporated by reference in their entirety as if fully set forth herein.

FIELD

This disclosure relates generally to a case for a medical device, such as an epinephrine (adrenaline) auto-injector, asthma inhaler, and the like.

BACKGROUND

Millions of Americans suffer from a potentially life-threatening from of allergy called anaphylaxis. Within seconds to minutes of the reaction, morbidity and mortality can ensue unless epinephrine is injected intramuscularly immediately. The most common cause of anaphylaxis is allergies due to foods but anaphylaxis can also occur with stinging insects (such as bees), latex and be due to unknown causes (idiopathic anaphylaxis.) The prevalence of anaphylaxis has risen dramatically over the last years for unclear reasons and continues to increase.

Most, if not all individuals diagnosed with anaphylaxis are prescribed injectable epinephrine (adrenaline), which can be life-saving and is as important as defibrillators but must be available immediately. Epinephrine auto-injectors are available via brands such as EpiPen™ Auvi-Q™, a generic injector manufactured by Lineage Therapeutics, or similar injectors such as those made in countries outside the United States.

The problem is that an auto-injector must be available on the spot. Most fatalities from anaphylaxis occur outside the home such that carrying an auto-injector on the person or adult attending the child is paramount.

Millions of other people suffer from other ailments that require a medical device, such as an asthma inhaler. These people also must have immediate access to their medical device.

In addition, most people carry a portable smartphone, belt, or the like, with them at all times. But carrying an auto-injector or other medical device separately is bulky and difficult and often the device is forgotten at home out of reach for immediate utilization.

SUMMARY

In view of the foregoing, there is a need for methods and apparatus for carrying a medical device.

Provided herein is a system for carrying a medical device, such as an epinephrine auto-injector that is both convenient and easy for users. Because most individuals now carry an electronic phone/smartphone, in some embodiments is disclosed is a system for allowing users to easily carry both their smartphone and their medical device.

In a related aspect, provided is method for carrying a medical device, such as an epinephrine auto-injector, without a smartphone.

As used herein, a smartphone can include, but is not limited to, an iPhone, Android phone, Blackberry, mobile phone, tablet, or any other portable handheld computing device that easily fits within a pocket.

As used herein, a medical device can include, but is not limited to an epinephrine auto-injector, an asthma inhaler, a diabetes devices, an albuterol inhaler, an Insulin pen, a lancet, a blood glucose meter, a blood glucose tester, a syringe, a thermometer, a sphygmomanometer, a pulse oximeter, a patch, a spray (such as a nasal spray), a hearing aid, glasses, contact lenses, eye drops, ear drops, lip balm, a pill, a pill holder, and the like.

Provided in some embodiments is a case that includes: a first pocket designed to contain a smartphone; a second pocket designed to contain a medical device; and a containment device for containing the medical device within the case.

In some embodiments, a method for carrying a medical device includes: providing a smartphone carrying case comprising a first pocket for a smartphone and a second pocket for a medical device; inserting the smartphone into the first pocket of the carrying case; inserting the medical device into the second pocket carrying case; transporting the carrying case with both the smartphone and the medical device; and removing the medical device from the carrying case.

In some embodiments, a medical device case is provided that includes: a container designed to contain a medical device; a locking cap that contains the medical device within the container; and an attachment that is designed to releasably attach the case to a secondary device.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE FIGURES

The present invention is illustrated by way of example, and not by way of limitation, in the figures of the accompanying drawings in which.

DETAILED DESCRIPTION OF THE DISCLOSURE

The following description and the drawings illustrate specific embodiments sufficient to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

As shown in the attached figures, embodiments comprising a carrying case for carrying a medical device such as an epinephrine auto-injector are disclosed.

In at least one embodiment, a dedicated protective pocket for the smartphone includes a form fitting pocket for the medical device. The pocket comprises plastic, rubber or any other material currently employed in the manufacturing of smartphone protectors, covers and/or housings.

In another embodiment, a carrying case includes a pocket designed to house a medical device and a pocket for holding the epinephrine auto-injector to the smartphone. The pocket can be just large enough to attach the medical device to the smartphone or slightly larger to hold additional items in addition to the medical device, such as instructions, money, credit cards, or the like.

An embodiment also shows how to deal with the issue of when the smartphone starts to overheat or gets hot. A protective material such as a layer of rubber or other non-conducting material is inserted in the pocket for the smartphone to protect the medical device from excessive heat that may be emitted by the smartphone.

The embodiments shown herein can be in multiple/different colors and patterns to be pleasing to the user. Other embodiments can provide for the skins that allow the outside color or pattern to be changed by the user without having to buy an entirely new carrying case. These skins can be changed at will by the user, such that every day, month, year, or the like, the user can alter the outside appearance of the carrying case.

Figure 1A:
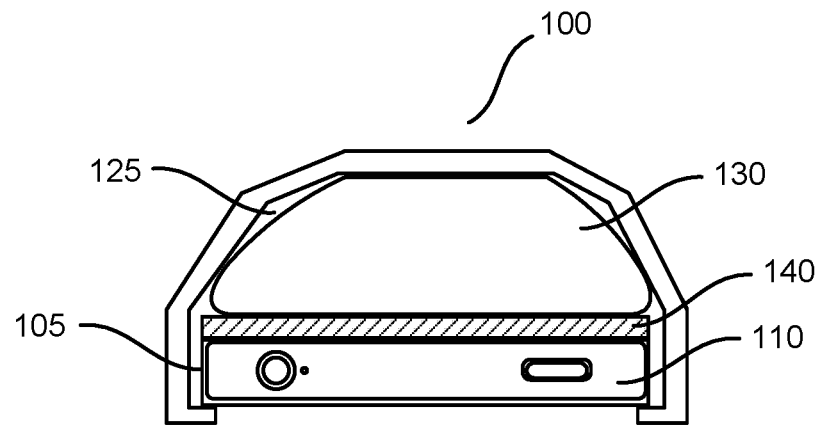
FIG. 1a is top view disclosing an embodiment of the present invention.

FIG. 1a shows a top view of an embodiment of a carrying case 100 of the present invention. The case 100 includes a first pocket 105 for the smartphone 110 (indicated as an iPhone™) and a second pocket 125 for the medical device 130 (indicated as Auvi-Q™). The first pocket 105 can be molded to fit the particular smartphone being used, such as being molded to fit an iPhone™, or can be a generic pocket designed to fit most smartphones. A rubber insert or other protective material 140 can be placed between the smartphone and the medical device to prevent the transmission of heat from the smartphone to the medical device. The protective material 140 can be just behind the smartphone 110 or can extend the entire length between the smartphone 140 and the medical device 130.

A containment device is used to keep the medical device 130 within a second pocket 125. The containment device can be, for example, a flap, a cover (such as a lid or cap), a plastic covering, a clip, a zippered cover, a snap, Velcro™, rubberized material within the pocket 125, or the like. Alternatively still, other devices can be used to containing the medical device 130 within the second pocket 125, including a child-proof lock, a locking mechanism that locks using a mechanical or digital device, a combination lock (such as one having 2, 3, 4 or more dials), a twisting mechanism, a pinch/push/and/or pull mechanism, a biometric lock, a touch ID lock, a voice-activated lock, a lock requiring a passcode, a lock requiring a geometric pattern to unlock, a lock requiring a pin or alpha-numeric passcode, or the like.

In another embodiment, the case includes a plastic material snugly enclosing the middle of the medical device 130 while the sides include C-shaped clips that attach the medical device to the smartphone, containing the medical device. The clips may or may not be adjustable via a ratchet, pinion or rack or cable-tie system to allow the tension to be adjusted to grip the medical device so as to mount it safely to the smartphone.

In one embodiment, a flap can be placed to cover the top of a medical device 130. The flap allows for the removal of the medical device. If a flap is used, one end of the flap can connect to the case using a snap, button, Velcro, magnets, ties, or the like. Alternatively, the flap can be zippered open and closed. When the medical device is to be removed, the user disconnects or opens the flap (such as by unsnapping it) and then is able to grasp the medical device from the case.

Some medical devices, such as an Auvi-Q™, are contained within its own housing. The entire Auvi-Q™ housing can be placed in the second pocket 125. When the user desires to remove the medical device 130, the medical device housing can remain in the second pocket with just the part of the medical device containing the medicine being removed. Alternatively, the entire medical device 130, including its own housing, can be removed.

The second pocket 125 can be of varying size or shape, depending on what medical device was desired to be contained within the pocket 125. Alternatively still, the pocket could be larger to allow other items to also be contained in the pocket, such as money, coins, credit cards, identification cards such as a driver's license, a condom, another medical device, bandages, candy, small pills, and the like. Alternatively still, the other items could be contained in a third pocket on the case 100.

Alternatively, the second pocket 125 can be designed to hold two or more medical devices. Alternatively still, the second pocket 125 can be designed to hold two medical devices and include a clip to connect the two medical devices (such as two EpiPen™ devices). In another embodiment, a graspable or gripping material is used within the case to allow for easier removal of the medical device from the case.

Alternatively, the bottom of the second pocket can have a hole. The hole can serve as a release mechanism whereby the user can insert his or her finger into the hole to push up on the medical device to release it from the second pocket 125. Other release mechanisms can be used to help secure and then remove the medical device to the case. These release mechanisms can include an area around the second pocket that allows the medical device to be grasped, a flap that covers the medical device that is opened when the medical device is to be removed (wherein the flap is releasably attached to the case to close, or just closes), a spring mechanism that uses the spring to push the medical device out (for example when a button is pushed), a pull tab to pull up on the medical device, a handle to grab the medical device, an open area in the pocket to grasp the medical device, or other mechanisms to remove the medical device.

In an alternative embodiment, the medical device is attached to an already existing case, such as a protective housing or cover. This embodiment includes a plastic material enclosing the middle of the epinephrine auto-injector while the sides of the case include clips, such as C-shaped clips, that attach the medical device to the smartphone. The clips could be adjustable via a ratchet, pinion or rack or cable-tie system that allows the tension to be adjusted to grip the medical device so as to mount it safely to the smartphone.

Figure 1B:
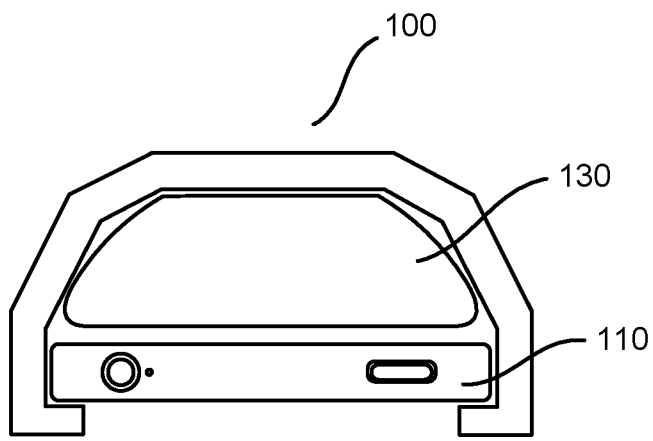
FIG. 1b is top view disclosing another embodiment of the present invention.

FIG. 1b shows an alternative embodiment where the medical device 130 rests on the back of the smartphone 110.

The case 100 can be designed such that the first and second pockets are connected, allowing the medical device and the smartphone to touch one another. In another embodiment, multiple pockets are used whereby each additional pocket holds another medical device.

Figure 2A:
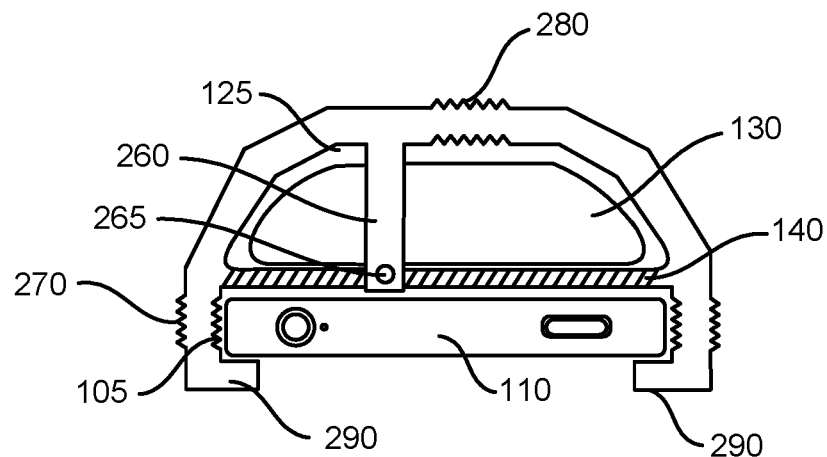
FIG. 2a is top view disclosing another embodiment of the present invention.

FIG. 2a shows an alternative embodiment where a clip 260 is used to keep the medical device 130 releasably attached to the smartphone 110 or in the second pocket 125. The clip 260 can use a snap 265, button, Velcro, zipper, magnets, ties, or the like. As discussed and shown in FIG. 2a, this can be accomplished with the second pocket 125 having a magnet 260 and the first pocket 105 having a magnet 265.

A tension 270 and 280 can be used to keep the medical device 130 connected to the smartphone 110. The tension 270 and 280 can be adjustable, such as in a horizontal or a vertical direction (or both). The tension can be adjusted using a ratchet system that is adjustable, cable or zip ties, bands (made out of for example rubber or elastic) or other clips. The ends of the attachment mechanism can include one or more lips 290 that include rubber tips to protect the smartphone from the attachment mechanism. The lips 290 may be used to keep the smartphone 110 in the first pocket 105.

In one embodiment, the tension 270 and 280 can be adjusted using a ratchet system to adjust the tension used to secure the medical device to the smartphone. The tension can be adjusted in multiple directions.

Figure 2B:
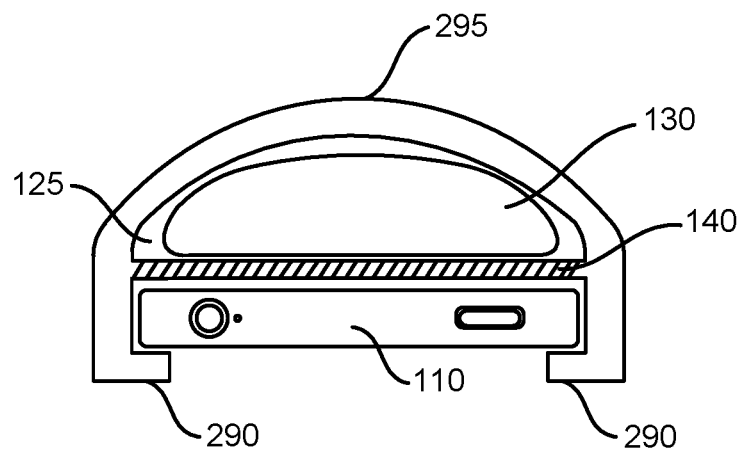
FIG. 2b is top view disclosing another embodiment of the present invention.

FIG. 2b shows an alternative embodiment where a band 295, such as made of a stretchable material like rubber or elastic, is used to secure the medical device 130 within the second pocket.

Figure 3:
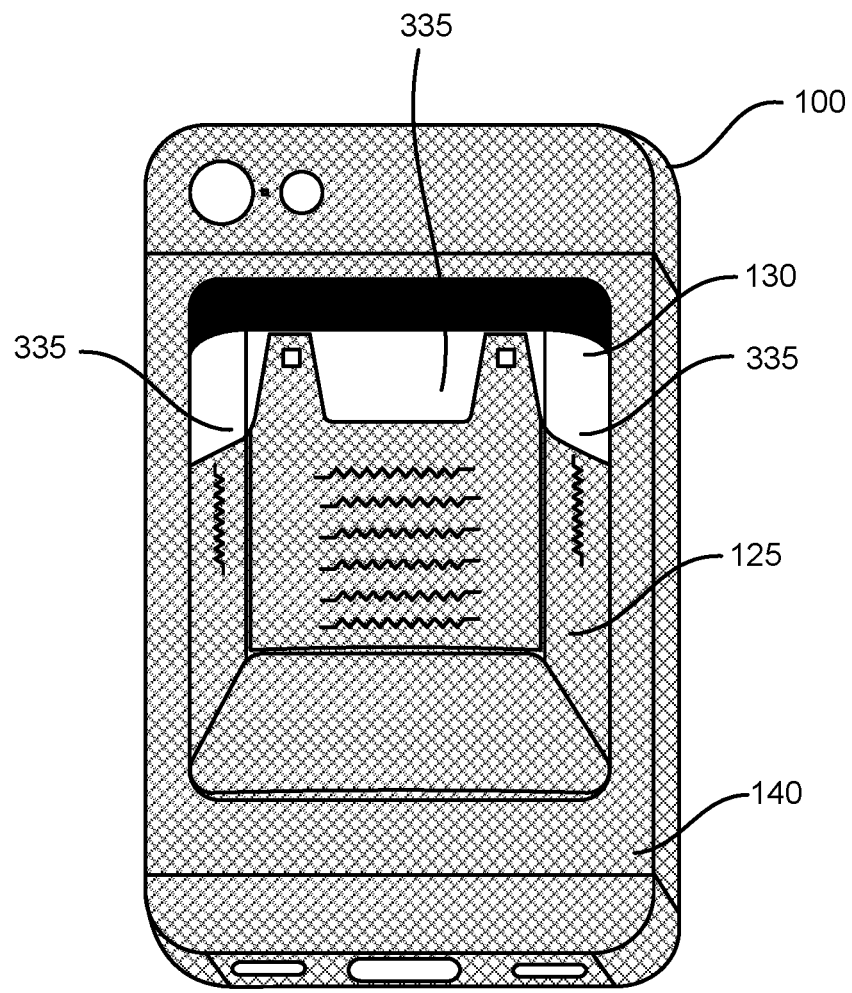
FIG. 3 is a rear view disclosing another embodiment of the present invention.

FIG. 3 shows a front view of an embodiment of a case of the present invention. The second pocket 125 includes three spaces 335 that allow the medical device 130 to be releasably grasped from the pocket 125. There can be one space, two spaces, four spaces, or any number of spaces in the pocket. The pocket can be specifically molded to fit a particular medical device, or a generic sized pocket. If the medical device is an Auvi-Q™, the pocket could be shaped to fit the Auvi-Q™. If the medical device is an asthma inhaler, the pocket could be shaped to fit the inhaler. If the medical device is an EpiPen™, the pocket could be shaped to fit the EpiPen™, and so on.

A protective sheet or cover 140 can be used between the second pocket and the smartphone, to protect the medical device from the smartphone, and the medical device from being subjected to excessive heat from the smartphone.

Figure 4:
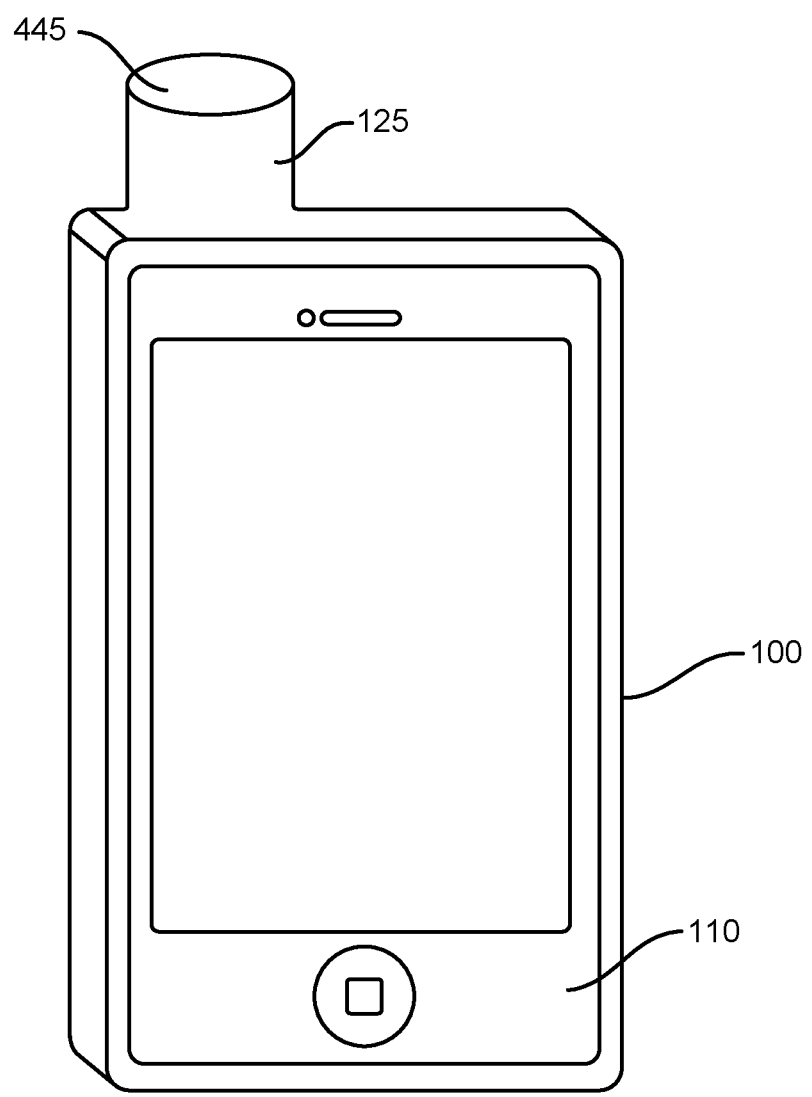
FIG. 4 is a front view of an embodiment of a case of the present invention.

FIG. 4 shows a front view of an embodiment of a case of the present invention that holds an EpiPen. A cover 445 lifts open to insert a carrier tube of an EpiPen. Alternatively, the cover can be the lid to the housing for the EpiPen carrier tube. In this embodiment, the EpiPen is held behind the smartphone although it could be in the front. When a user desires to remove the EpiPen from the case 100, the cover 445 from the case can be removed or flipped open. Then the EpiPen is removed. The cover 445 prevents the EpiPen from falling out while the case is in use. Alternatively, elastic or other stretchable material can be used to help contain the EpiPen in the pocket. Alternatively, there is no cover to the case and the EpiPen is contained in the case by friction caused by the case being form fitted just to fit the EpiPen, such that the EpiPen is released by grasping on the EpiPen by the user and pulling up—in such an instance the user would remove the EpiPen, flip open the cover to the carrier tube, and then use the device. Alternatively still, a hole or pushing mechanism is on the underside of the pocket holding the EpiPen such that user pushes his or her finger through the hole to push up on the EpiPen to release it from the case.

Figure 5:
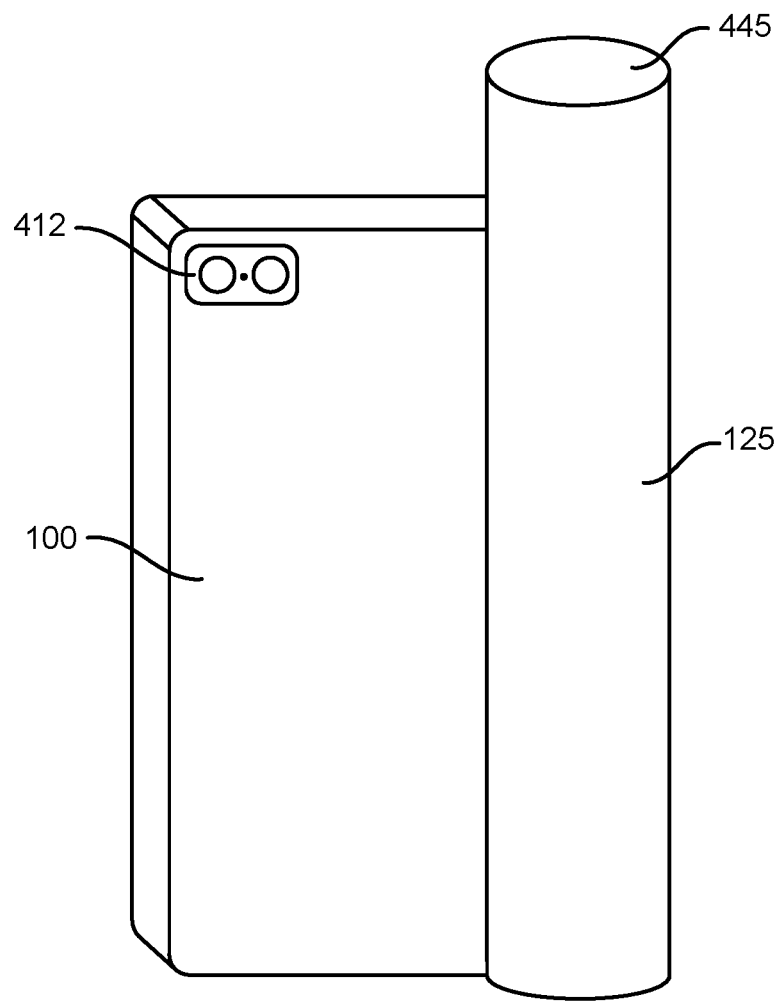
FIG. 5 is a rear view of an embodiment of a case of the present invention.

FIG. 5 shows a rear view of an embodiment of a case of the present invention that holds an EpiPen. The lens 412 of the smartphone is shown through the case 100. The pocket 125 holding the EpiPen is shown. Again, a cover 445 can be used that flips open when the EpiPen is to be inserted into the case or removed from the case.

Figure 6A:
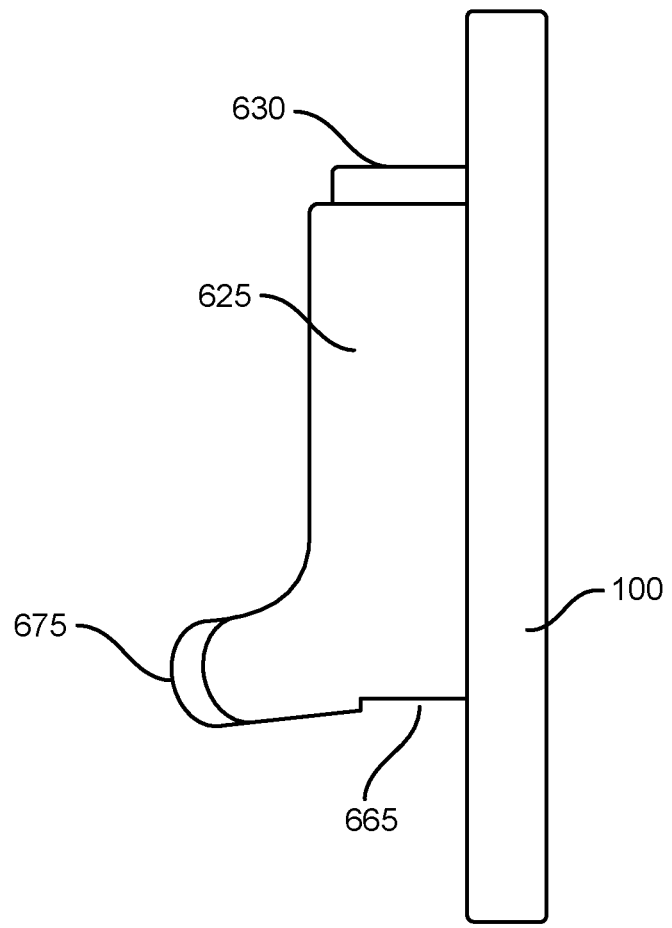
FIG. 6a shows a side view of an embodiment of a case of the present invention that holds a medical device.

FIG. 6a shows a side view of an embodiment of a case 100 of the present invention that holds an inhaler medical device 630. The pocket 625 that holds the inhaler may be specifically shaped and designed to fit snuggly around the inhaler. A hole 665 can be used on the bottom of the pocket to help remove the medical device. Alternatively, the pocket can be less snug such that other items such as money, instructions, or a credit card could also be inserted into the pocket.

In one embodiment, when the medical device 630 is needed, it is pulled out of the pocket 625. In another embodiment, a cap 675 is releasably attached to the pocket 625 such that the user can use the medical device 630 without having to remove the medical device 630 from the pocket 625. In another embodiment, there is no cap 675.

In one embodiment, the medical device 630 is an inhaler. The cap of the inhaler is removed prior to inserting it into the pocket 625. When needed to be used, the cap 675 of the pocket 625 is opened and the inhaler is used directly from the pocket 625. Alternatively, the inhaler is removed from pocket 625 prior to use.

Figure 6B:
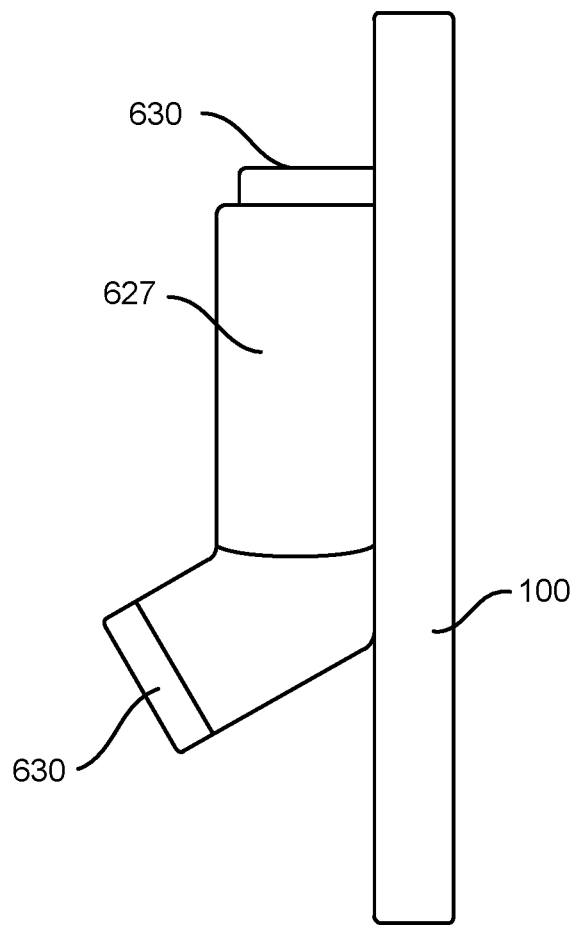
FIG. 6b shows a side view of an embodiment of a case of the present invention that holds a medical device.

FIG. 6b shows a side view of another embodiment of a case 100 of the present invention that holds an inhaler medical device 630. Pocket 627 can comprise a stretchable material such as elastic or a rubber band that contains the medical device 630 within the pocket. The stretchable material can be affixed to the case or releasably attached to the case, using Velcro, buttons, snaps, a zipper, or the like. In this embodiment, the medical device 630 can be used while still in pocket 627 (such as by removing the inhaler's cap and using the inhaler while contained in pocket 627) or alternatively, the medical device 630 can be removed from pocket 627 and then used.

Figure 7:
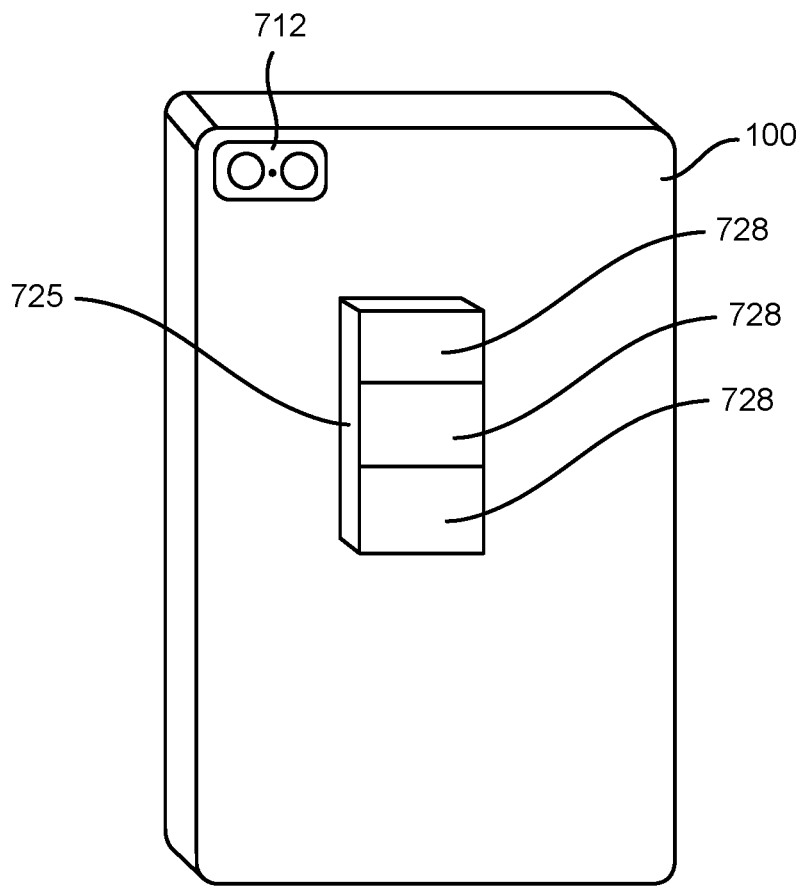
FIG. 7 shows a rear view of an embodiment of a case of the present invention that holds at least one pill.

FIG. 7 shows a rear view of an embodiment of a case of the present invention that includes a container 725 that holds at least one pill. The lens 712 of the smartphone is shown through the case 100. The at least one pill can be a number of pills or just one pill for an emergency. The at least one pill can be a medical pill, a vitamin, a supplement, or the like. At least one pill compartment 725 is used to hold the pills. The at least one compartment 725 holding the at least one pill can be, for example, on the side or back of the case. If there are multiple compartments 728, each can hold a single pill or multiple pills. The multiple compartments 728 can be labeled, for example, AM, PM, Evening, Noon, or the like. The labels can be removable and changeable. The compartment 725 can be releasably attached to the case, using Velcro, buttons, snaps, a zipper, or the like. Each compartment 728 can have a snap lid or other type of cover to hold in the pill. The pill compartment 725 can be used in conjunction with the second pocket for holding a medical device, or it can be used without a second pocket for holding a medical device. In other words, the at least one compartment 725 can be used with or without a pocket for holding another medical device.

In one embodiment, the medical device can contain a Blue-tooth emitter. Alternatively, the Blue-tooth emitter is attached to the medical device. The emitter allows a user to know if the case contains or does not contain the medical device. In one embodiment, a smartphone app is used to determine the proximity of the medical device to the case or smartphone. For example, the app can be used to communicate to a user once the medical device (containing the Blue-tooth emitter) is further than a specified distance. This allows the user to make sure he or she does not leave home or some other area (such as work or a restaurant) without the medical device in the case. An example of the Blue-tooth emitter is the Tile™, made by Tile Inc.

The case can be made of a variety of different materials, such as plastic, rubber, wood, a composite, porcelain, mother of pearl, metal, or the like.

Figure 8:
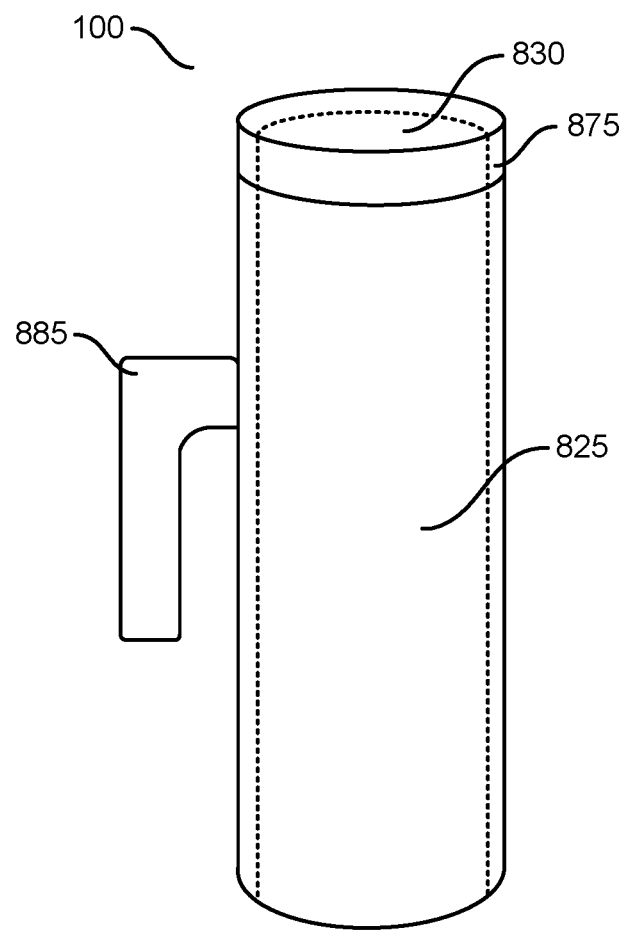
FIG. 8 shows an embodiment of a case of the present invention.

In another embodiment, case 100 contains the medical device but is not attached to a smartphone, rather instead to a belt, helmet or other location. FIG. 8 shows an embodiment of a case 100 of the present invention. The case 100 includes a container 825. The container 825 holds the medical device 830. The container 825 includes an attachment 885 that allows the container to be releasably attached to a secondary device, such as a smartphone, belt, helmet or the like. The attachment 885 can be a belt clip, a belt loop, a strap, an adhesive, a snap, a button, Velcro, a magnet, a tie, or the like.

The container 825 further comprises a locking cap 830. The locking cap 830 is designed to contain the medical device and keep the medical device within the case 100. It also prevents children from accessing the medical device without adult supervision, and/or prevents unwanted access to the medical device.

The locking cap 830 can be a child-proof cap, such as a twist and push or twist and pull locking cap. The locking cap 830 can alternatively be a locking mechanism that locks using a mechanical or digital device, a combination lock (such as one having 2, 3, 4 or more dials), a twisting mechanism, a pinch/push/and/or pull mechanism, a biometric lock, a touch ID lock, a voice-activated lock, a lock requiring a passcode, a lock requiring a geometric pattern to unlock, a lock requiring a pin or alpha-numeric passcode, or any other similar method described herein.

The smartphone can include a computer having a display device for displaying information to the user, a keyboard, a pointing device (e.g., a mouse or a trackball), and/or a touchscreen by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. Similarly, elements located on the front, back, side, top, or bottom of an embodiment or implementation are to be understood as relatively positioned, unless otherwise specified. Other embodiments can be within the scope of the claims.

This application is intended to cover any variations, uses or adaptations of the invention following, in general, the principles of the invention, and including such departures from the present disclosure as come within known and customary practice within the art to which the invention pertains. The foregoing description of specific embodiments reveals the general nature of the disclosure sufficiently that others can, by applying current knowledge, readily modify and/or adapt the system and method for various applications without departing from the general concept. Therefore, such adaptations and modifications are within the meaning and range of equivalents of the disclosed embodiments. The phraseology or terminology employed herein is for the purpose of description and not of limitation.

What is claimed is:

1. A case comprising:
   a first pocket configured to contain a smartphone, wherein the first pocket comprises a first magnet;
   a second pocket adjacent to the first pocket and configured to contain a medical device, wherein the second pocket is form-fitted to be in the shape of the medical device and not elastic;
   wherein the second pocket comprises a second magnet that magnetically and releasably connects the first pocket to the second pocket using the first and second magnets;
   wherein the second pocket is configured to be disengaged from the first pocket; and
   wherein the second pocket is configured to be releasably connected to a secondary device other than the smartphone, wherein the second pocket is configured to be connected to the secondary device using the second magnet.

2. The case of claim 1, further comprising a protective material between the first pocket and the second pocket, wherein the protective material is configured to protect the medical device when the smartphone becomes hot, and further wherein the medical device is selected from the group consisting of an epinephrine auto-injector, an inhaler, and at least one pill.

3. The case of claim 1 further comprising a Bluetooth emitter that is configured to allow the smartphone to communicate with the medical device.

4. The case of claim 1 wherein the medical device is an epinephrine auto-injector and the second pocket is molded to fit the epinephrine auto-injector.

5. The case of claim 4, wherein the second pocket is configured to contain two epinephrine auto-injectors.

6. The case of claim 1, wherein the medical device is contained within the second pocket by friction.

7. The case of claim 1, wherein the secondary device is a belt or helmet.

8. The case of claim 1, wherein a pill compartment is connected to the second pocket.

9. The case of claim 8, wherein the pill compartment comprises at least one label that is removably attached to the pill compartment.

10. The case of claim 1, wherein the second pocket comprises a pill compartment.

11. The case of claim 8, wherein the pill compartment is releasably attached to the second pocket.

12. A method for carrying a medical device comprising:
   providing a smartphone carrying case comprising a first pocket for a smartphone and a second pocket for a medical device, wherein the first pocket comprises a first magnet and the second pocket comprises a second magnet;
   inserting the smartphone into the first pocket of the carrying case, wherein the first pocket contains the smartphone;
   inserting the medical device into the second pocket, wherein the second pocket is form-fitted to be in the shape of the medical device and not elastic, and further wherein the medical device is selected from the group consisting of an epinephrine auto-injector, an inhaler, and at least one pill;

magnetically connecting the second pocket to the first pocket by connecting the first magnet to the second magnet;

transporting the carrying case with both the smartphone and the medical device;

disconnecting the second pocket from the first pocket; and magnetically connecting the second pocket to a secondary device that is other than the smartphone using the second magnet.

13. The method of claim 12, wherein the medical device is the epinephrine auto-injector and is substantially flat on at least four sides, and the second pocket is molded to fit the epinephrine auto-injector.

14. The method of claim 12, further comprising:
opening a pill compartment connected to the second pocket; and
inserting a pill in the pill compartment.

15. The method of claim 14, further comprising:
disconnecting the pill compartment from the second pocket; and
reconnecting the pill compartment to the second pocket.

16. The method of claim 14, further comprising:
inserting a first label on the pill compartment;
removing the first label from the pill compartment; and
inserting a second label on the pill compartment in the place where the first label was previously attached to the pill compartment.

17. A case comprising:
a first pocket configured to contain a smartphone, wherein the first pocket is configured to protect the smartphone;
a second pocket configured to contain a medical device, wherein the medical device is selected from the group consisting of an epinephrine auto-injector, an inhaler, and at least one pill;
wherein the first pocket comprises a first magnet;
wherein the second pocket comprises a second magnet;
wherein the second pocket is form-fitted to be in the shape of the medical device and not elastic;
a release mechanism that is configured to release the medical device from the case;
a protective material between the first pocket and the second pocket;
wherein the second magnet of the second pocket magnetically and releasably connects the first pocket to the second pocket using the first and second magnets; and
wherein the second pocket is configured to be disengaged from the first pocket and configured to be releasably connected to a secondary device other than the smartphone using the second magnet.

18. The case of claim 17, wherein the medical device is contained within the second pocket by friction.

19. The case of claim 17, wherein the second pocket is a pill compartment.

20. The case of claim 17, wherein a pill compartment is connected to the second pocket, and the pill compartment comprises at least one label that is removably attached to the pill compartment.

\* \* \* \* \*